United States Patent
Wolf

(10) Patent No.: US 7,166,201 B2
(45) Date of Patent: *Jan. 23, 2007

(54) SELF-CONDENSING PH SENSOR

(75) Inventor: Erich Wolf, Vista, CA (US)

(73) Assignee: Sierra Medical Technology, Poway, CA (US)

( * ) Notice: Subject to any disclaimer, the term of this patent is extended or adjusted under 35 U.S.C. 154(b) by 220 days.

This patent is subject to a terminal disclaimer.

(21) Appl. No.: 10/725,920

(22) Filed: Dec. 1, 2003

(65) Prior Publication Data
US 2005/0115834 A1 Jun. 2, 2005

(51) Int. Cl.
G01N 27/403 (2006.01)

(52) U.S. Cl. ....................... 204/433; 204/435
(58) Field of Classification Search ................ 204/433, 204/435; 205/787.5
See application file for complete search history.

(56) References Cited

U.S. PATENT DOCUMENTS

| 3,742,594 | A | * | 7/1973 | Kleinberg | ............... | 29/592.1 |
|---|---|---|---|---|---|---|
| 3,880,737 | A | * | 4/1975 | Brunt | ............... | 204/420 |
| 3,946,726 | A | | 3/1976 | Pikui | | |
| 3,991,304 | A | | 11/1976 | Hillsman | | |
| 4,366,821 | A | | 1/1983 | Wittmaier et al. | | |
| 4,913,793 | A | * | 4/1990 | Leonard | ............... | 204/433 |
| 5,042,501 | A | | 8/1991 | Kenny et al. | | |
| 5,069,220 | A | | 12/1991 | Casparie et al. | | |
| 5,081,871 | A | | 1/1992 | Glaser | | |
| 5,140,993 | A | | 8/1992 | Opekun, Jr. et al. | | |
| 5,147,524 | A | * | 9/1992 | Broadley | ............... | 205/787.5 |
| 5,174,959 | A | | 12/1992 | Kundu et al. | | |
| 5,213,109 | A | | 5/1993 | Susi | | |
| 5,265,595 | A | | 11/1993 | Rudolph | | |
| 5,327,901 | A | | 7/1994 | Delente | | |
| 5,346,606 | A | * | 9/1994 | Christner et al. | ............... | 205/787.5 |
| 5,361,772 | A | | 11/1994 | Murnick et al. | | |
| 5,432,094 | A | | 7/1995 | Delente | | |
| 5,465,728 | A | | 11/1995 | Philips | | |
| 5,645,049 | A | | 7/1997 | Foley et al. | | |
| 5,676,154 | A | | 10/1997 | Pettersson | | |
| 5,795,787 | A | | 8/1998 | Silkoff et al. | | |
| 5,826,577 | A | | 10/1998 | Perroz, Jr. et al. | | |
| 5,857,460 | A | | 1/1999 | Popitz | | |
| 5,922,610 | A | | 7/1999 | Alving et al. | | |
| 5,962,335 | A | | 10/1999 | Katzman | | |
| 6,010,459 | A | | 1/2000 | Silkoff et al. | | |
| 6,033,368 | A | | 3/2000 | Gaston, IV et al. | | |
| 6,053,874 | A | | 4/2000 | Kharitonov et al. | | |
| 6,067,983 | A | | 5/2000 | Stenzler | | |
| 6,180,414 | B1 | | 1/2001 | Katzman | | |
| 6,186,958 | B1 | | 2/2001 | Katzman et al. | | |
| 6,213,955 | B1 | | 4/2001 | Karakasoglu et al. | | |
| 6,221,026 | B1 | | 4/2001 | Philips | | |
| 6,312,390 | B1 | | 11/2001 | Philips | | |
| 6,398,739 | B1 | | 6/2002 | Sullivan et al. | | |
| 6,419,634 | B1 | | 7/2002 | Gaston, IV et al. | | |

(Continued)

Primary Examiner—Kaj K. Olsen
(74) Attorney, Agent, or Firm—Michael Klicpera

(57) ABSTRACT

The present invention pertains to an apparatus and a means of constructing a pH sensor that can detect changes in pH levels of humidified gases and liquid samples. When electronically connected to a computerized or analog display means, sensitive quantitative measurements can be obtained. Given the construction of current pH devices available today, there is a need in the field for a novel, miniaturized, self-condensing pH probe that can be used in fluid or humidified gases.

21 Claims, 2 Drawing Sheets

U.S. PATENT DOCUMENTS

| | | |
|---|---|---|
| 6,479,019 B1 | 11/2002 | Goldstein et al. |
| 6,491,643 B1 | 12/2002 | Katzman et al. |
| 6,540,691 B1 | 4/2003 | Philips |
| 6,582,376 B1 | 6/2003 | Baghdassarian |
| 6,585,661 B1 | 7/2003 | Hunt et al. |
| 6,599,253 B1 | 7/2003 | Baum et al. |
| 6,612,306 B1 | 9/2003 | Mault |
| 6,653,842 B1 * | 11/2003 | Mosley et al. .............. 324/446 |
| 2003/0013695 A1 | 1/2003 | Hunt et al. |
| 2003/0023389 A1 | 1/2003 | Rothe et al. |
| 2003/0134427 A1 | 7/2003 | Roller et al. |

* cited by examiner

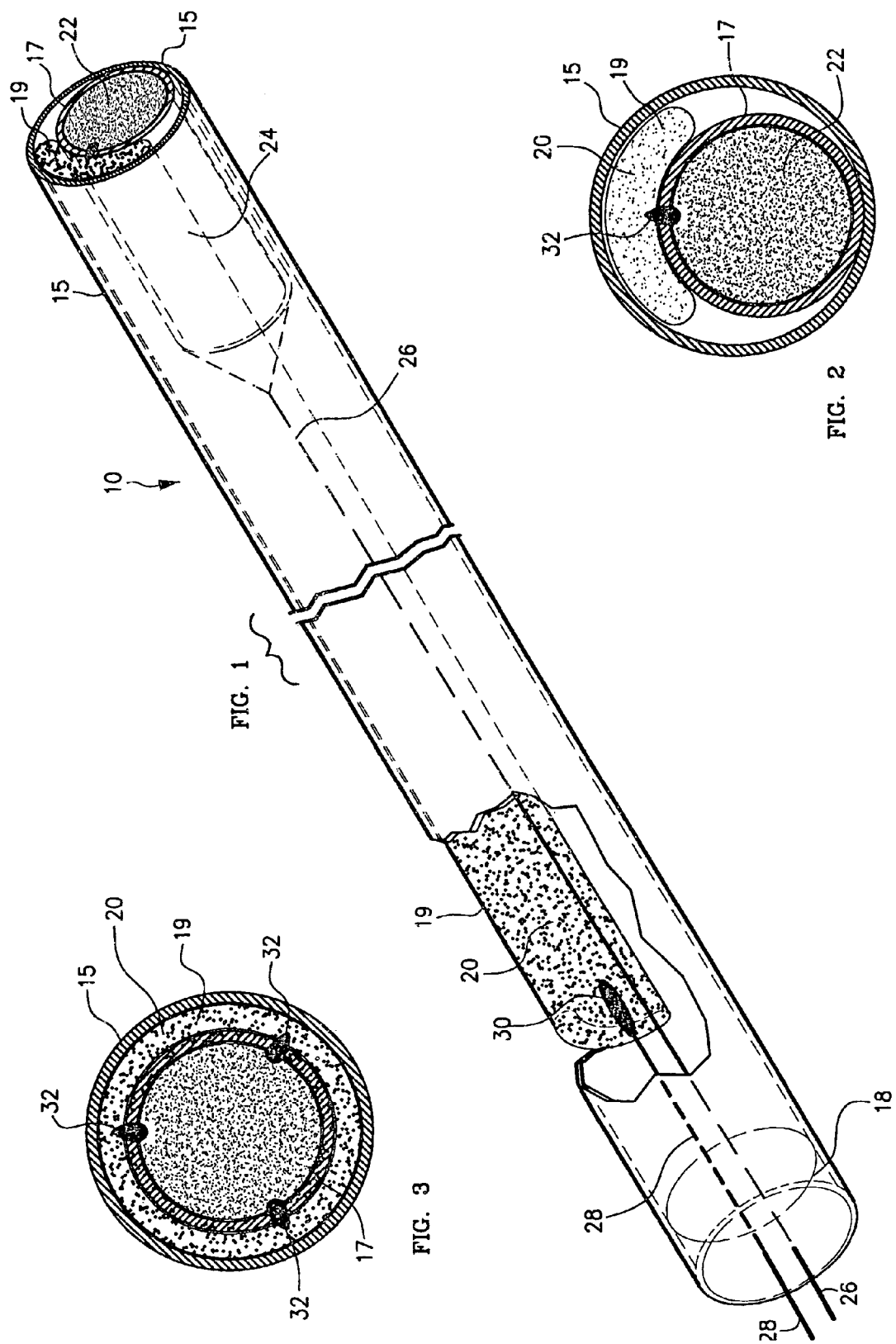

SELF-CONDENSING PH SENSOR

FIELD OF THE INVENTION

The present invention relates to the field of pH sensors and monitoring pH levels of fluids and humidified gases. More specifically, it details the integration of known pH sensor materials to achieve a novel and compact pH sensor probe. Because of the proximity and orientation of the sensor's elements, it is able to self-condense and monitor pH changes of humidified gases as well as liquids.

BACKGROUND OF THE INVENTION

Development of the modern pH scale was first discussed in a 1909 paper by a Danish scientist named Soren Sorenson. Sorenson proposed that the actual degree of acidity should be rationally measured by hydrogen ion concentration and created the pH scale for expressing these levels. Today, it is measured on a scale of 0 to 14 with the lower numbers being more acidic, the higher numbers more basic, and 7 as the neutral value. In chemical terms, pH means the negative log of the concentration of protons in solution.

A commonly used tool for identifying pH of liquids is the use of pH papers or indicators. These papers, when exposed to a liquid media, will change color as the pH level varies. These indicators are convenient to use, but have limitations on their accuracy, and can be difficult to interpret correctly when used with a colored or murky sample.

To obtain more accurate readings, one typically relies on electronic pH measurement equipment. This equipment consists of three parts: a pH measuring electrode, a reference electrode, and a high input impedance meter. The pH electrode can be thought of as a battery, with a voltage that varies with the pH of the measured solution. Commonly, the pH measuring electrode is a relatively large glass bulb with a hydrogen ion sensitive coating. This coating will create a millivolt output that varies with changes in relative hydrogen ion concentration inside and outside of the bulb. The reference electrode can consist of a combination of metals and chemicals that create a millivolt output that does not vary with changes in hydrogen ion concentration.

In addition to coated glass, there exist many other types of pH sensing electrodes. Metallic substances such as antimony, that exhibit a change in electrical potential when immersed in different pH fluids, can be used. Other materials such as specially formulated polymers have also been used successfully.

Semiconductor technology can be used to create transistors that can sense pH changes in fluid. Ion Sensitive Field Effect Transistors ("ISFET's") typically exhibit improved repeatability and precision over a wide dynamic range, though at a considerably higher cost.

Other state of the art devices utilize optical sensing, capacitive sensing, and nanotechnology.

SUMMARY OF THE INVENTION

The present invention pertains to an apparatus and a means of constructing a pH sensor that can detect changes in pH levels of humidified gases and liquid samples. When electronically connected to a computerized or analog display means, sensitive quantitative measurements can be obtained. Given the construction of current pH devices available today, there is a need in the field for a novel, miniaturized, self-condensing pH probe that can be used in fluid or humidified gases.

The present invention comprises a multi-tubular design with the outer tubular member housing a silver chloride reference element, an ion conducting mesh, and an antimony sensor plug isolated in an inner tubular member that is co-linearly or coaxially configured with the outer tubular member.

These and other features, aspects and advantages of the present invention will become better understood with reference to the following descriptions and claims.

BRIEF DESCRIPTION OF THE DRAWINGS

FIG. 1 is a partially sectional side view of the sensor apparatus demonstrating in detail of the orientation and components of the pH sensing means.

FIG. 2 is top view of the terminal end of the sensor apparatus demonstrating the offset co-linear position of the antimony sensor and the reference wick with a condensed droplet electrically bridging the antimony sensor and the reference wick.

FIG. 3 is top view of the terminal end of another embodiment sensor apparatus demonstrating the position of the reference wick surrounding an inner coaxially positioned tubular member containing the antimony sensor with several condensed droplets electrically bridging the antimony sensor and the reference wick.

DESCRIPTION OF THE PREFERRED EMBODIMENT

Figure 5:
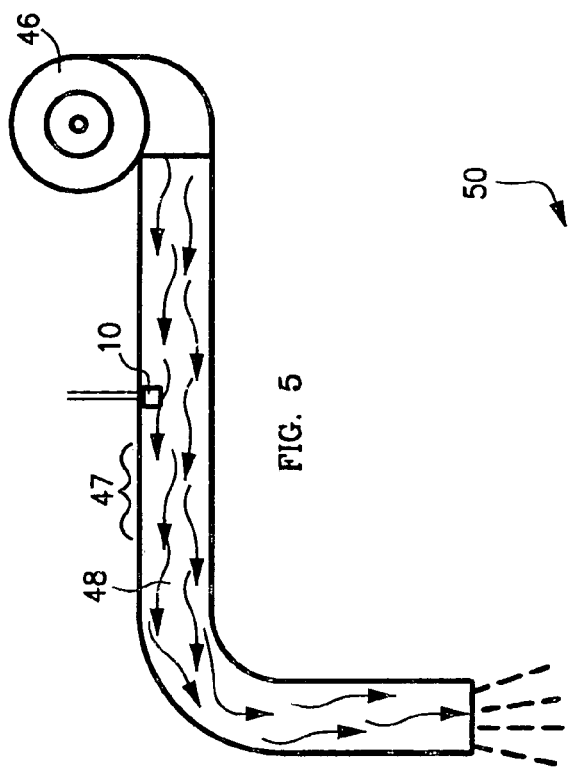
FIG. 5 is the present invention sensor being used in an example humid gaseous environment.

The present invention pertains to an apparatus and a means of constructing a pH sensor that can detect changes in pH levels of humidified gases and liquid samples. When electronically connected to a computerized or analog display means, sensitive quantitative measurements can be obtained. Given the construction of current pH devices available today, there is a need in the field for a novel, miniaturized, self-condensing pH probe that can be used in fluid or humidified gases.

FIG. 1 illustrates the present invention consisting of a system 10 is comprised of several components. As shown in this Figure, a typical partially sectional side view of the sensor apparatus demonstrates the orientation and components of the pH sensor.

The sensor apparatus 10 consists of an outer tubular member 15 that is usually fabricated by an extrusion or dip coating process using a variety of polymeric materials including polyimide, polyethylene, polypropylene, polyvinyl chloride, polystyrene, ABS, nylon, delrin, polyethylene terephthalate (PET) or polytetrafluoroethylene (PTFE). The outer tubular member 15 generally has an outside diameter in the range of 0.010" to 0.050", and preferably between 0.020" and 0.030". Its wall thickness is typical for its diameter and generally is in the range of 0.00025" to 0.0015" and preferably between 0.0005" and 0.001". The outer tubular member may include a coating specific for certain applications, e.g. protection from acid environments.

Co-linearly or coaxially aligned within the outer tubular member 15 is an inner tubular member 17 that is also usually fabricated by an extrusion or dip coating process using a variety of polymeric materials including polyimide, polyethylene, polypropylene, polyvinyl chloride, polystyrene, ABS, nylon, delrin, polyethylene terephthalate (PET) or polytetrafluoroethylene (PTFE). The inner tubular member has an outside diameter smaller than the outer tubular member and generally is in the range of 0.015" to 0.030", and preferably between 0.020" and 0.028". Its wall thickness is typical for its diameter and generally is in the range of 0.00025" to 0.0015" and preferably between 0.0005" and 0.001".

Located at the terminal end of the inner tubular member 17 is an antimony sensor 24 having a surface area 22. The antimony sensor 24 is generally 99% pure and free from significant contaminates. The Applicant contends that the antimony sensor could be replaced with other metallic substances like antimony that exhibit a change in electrical potential when immersed in different pH fluids. Furthermore other potential materials such as specially formulated polymers, semiconductor technology, Ion Sensitive Field Effect Transistors ("ISFET's"), optical sensing, capacitive sensing, and nanotechnology could be employed.

The antimony sensor 24 is engaged at its proximal end to an electronic communication means 26. Typically electrical wire 26 has an internal core comprises an electrically conductive metallic material that is encased by a nonconductive jacket. The means of engagement typically employs standard soldering technology and can be supported by a variety of means to provide strain relief. The surface 22 of the antimony sensor plug 24 defines the distal terminal boundary of the sensor and is the surface that is exposed to liquid or humid gaseous environments.

Located proximally from a range of 1–8 centimeters from the proximal end of the antimony sensor 24, and preferably 3–5 centimeters, is a reference element 30. Said reference element 30 is primarily composed of a silver core surrounded with a coating of silver chloride. Technology of dipping a silver core in a high temperature bath of silver chloride to produce the silver chloride coating is employed in the present invention. The resulting coating generally is 0.0001" to 0.001" in thickness, and preferably 0.0020" to 0.005". Reference element 30 is engaged to an electrical communication means 28, e.g. typical wire that extends to the proximal end of the outer tubular member 15 and can terminate in a typical electrical connector (not shown). An adhesive or polymer plug 18 can be placed in a proximal position to the reference element 30 that is engaged to the outer tubular member 15 which provides support electrical communication means 26 and 28 and proximal sealing of the outer tubular member 15.

A reference wick 20 is located between the inside surface of the outer tubular member 15 and the outer surface of the inner tubular member 17. In one embodiment (see FIG. 2), the inner tubular member 17 is coaxially offset with the outer tubular member 15. The reference wick 20 partially surrounds the inner tubular member 17 where the area of the offset coaxial design is large enough to contain the fabric or mesh configuration of the reference wick 20. As discussed in more detail below, reference wick 20 has a mesh or fibrous configuration which functions to entrain or retain an ion conducting fluid 19. As the mesh or fibrous configuration is compacted, less ion conduction fluid 19 can be entrained or retained. Reference wick 20 is physically separated from the antimony sensor 24 by the wall of inner tubular member 17. It is importance to the present invention that the reference wick 20 does not engage or contact the antimony sensor 24 at any point. The reference wick 20 can be fabricated from a cellulose base material, polymeric material, cotton or Hytrel (thermoplastic polyester elastomer) material which has a weave or mesh design which facilitates wicking and is compatible with the ion conduction fluid 19. One example of a material for the reference wick 20 is a polyester fabric mesh. The reference wick 20 functions as a plurality of capillary tubes which transport electrical ions between the antimony sensor 24 and reference element 30.

The reference wick 20 is impregnated with an ion conduction fluid 19. Typical conduction fluids include those that contain sodium chloride or potassium chloride and water. One example that can be used with the sensor is a cellulose base gel that is incorporated with a 2–10 percent, with a preferred range of 3–5 percent, solution of sodium chloride and water. Other materials that can function as the reference wick 20 with an ion conduction fluid 19 include ion carrying gels, hydrogels, and excipients. These gels, hydrogels, and excipients aid in reducing the diffusion of contaminants into the reference element 30.

FIG. 2 is top view of the terminal end of the sensor apparatus 10 demonstrating the offset coaxial position of the antimony sensor 24 and the reference wick 20 with a condensed droplet 32 electrically bridging the antimony sensor 24 and the reference wick 30. The sensor has self-condesing properties due to its small mass and capability of rapidly changing temperature. Also, the antimony sensor and the reference element are present on a single external surface on the disyal end of the device which allows for a droplet of condensed liquid to create an electrical bridge, as shown in FIGS. 2 and 3. The pH of the droplets can then be mesured, As an example (FIG. 6), when the present invention self-condensing sensor is used in conjunction with a system to mesure a patient's breath, the terminal portion of the device can rapidly cgange temperature in response to the inhalation and exhalation cycles of the patient. During inhalation, the external surface cools below the dew point of exhaled breath. When moist exhaled breath comes in contact with the external surface, passive condensing of droplets forms on the external surface without the assistance of any peripheral cooling means. The sensor 10 functions as an electric cell or battery where chemical energy is converted into electrical energy. The sensor utilizes the potential difference that exists between the sensor's different elements: the antimony sensor 24 and silver chloride reference 30. When a condensed droplet joins the antimony surface 22 with the reference wick 20, a voltage potential is created between the antimony sensor 24 and the reference element 30. This voltage potential changes relative to the reference element 30 depending on the pH of the liquid that the sensing elements are exposed to. Therefore, by monitoring the potential difference that exists between the antimony sensor 24 and the silver chloride reference 30, the pH of the condensed droplet can be accurately measured.

FIG. 3 is top view of the terminal end of another embodiment sensor apparatus demonstrating the position of the reference wick 20 surrounding an inner coaxially positioned tubular member 17 that contains the antimony sensor 24. In this embodiment, there is no offset between the coaxially positioned tubular members and the inner tubular member 17. Inner tubular member 17 is centered within outer tubular member 15 with reference wick 20 completely surrounding the inner tubular member 17. This embodiment has the advantage that any droplet which condenses along the circumference of the inner tubular member 17, can potentially form a bridge or junction between the antimony sensor 24 and the silver chloride reference 30. Several condensed droplets 32 are shown in FIG. 3 to electrically bridge between the antimony sensor 24 and the reference wick 20. In this particular situation, the average pH of all three droplets would be represented in the potential difference and measured by the sensor apparatus 10.

Figure 4:
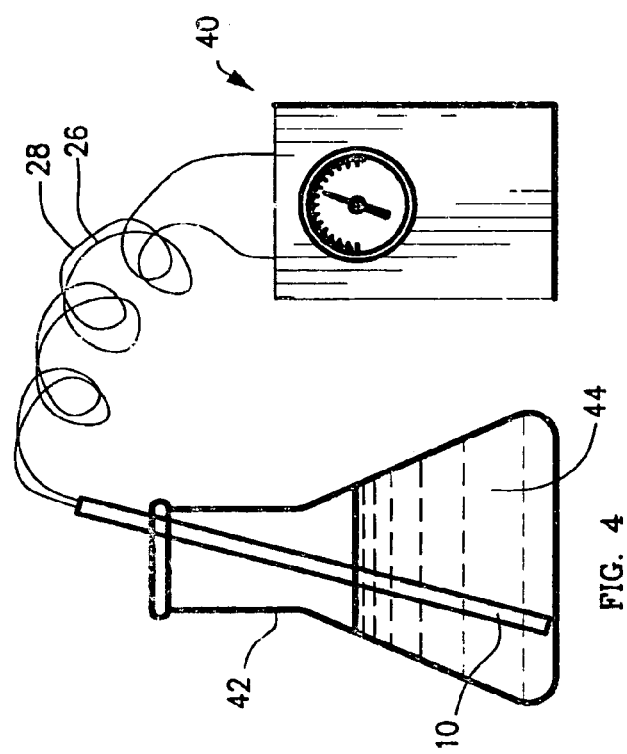
FIG. 4 is the present invention sensor being used in an example liquid environment.

FIG. 4 is the present invention sensor 10 being used in an example liquid environment. Sensor apparatus 10 is shown immersed within a fluid 44 contained in a flask 42. Extending from the sensor 10 are the antimony sensor electrical communication means 26 and reference element 30 electrical communication means 28 which are connected to a display/processing means 40. The sensor can provide an immediate reading of the pH level of the fluid 44 or the sensor could be used to monitor pH of the fluid continuously over time to detect changes in the pH.

FIG. 5 is the present invention sensor 10 being used in an example humid gaseous environment. Shown in FIG. 5 is pump 46 forcing humid gas 48 through a passageway 47. Sensor apparatus 10 is positioned within the passageway and exposed to the humid gas to provide a means for continuously monitoring the pH of the gas.

Figure 6:
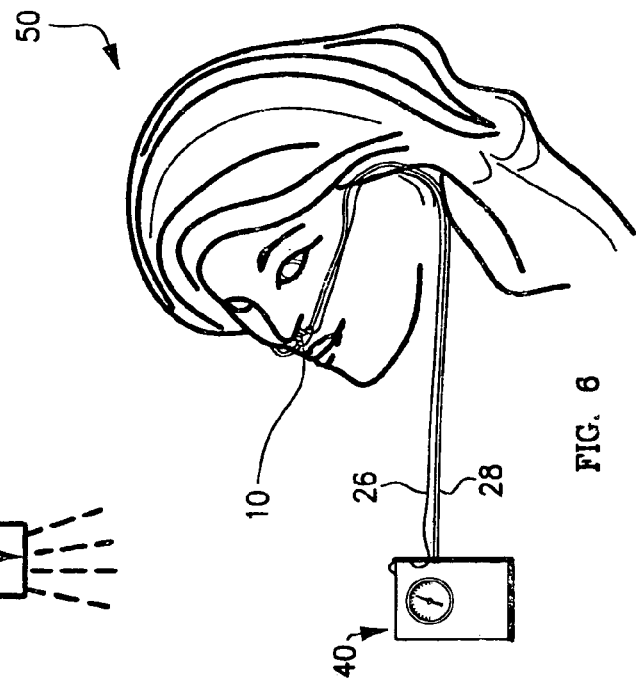
FIG. 6 is the present invention sensor being used in an example clinical application.

FIG. 6 is the present invention sensor being used in an example clinical application. In FIG. 6, sensor apparatus 10 is shown attached to a mask or nasal cannula positioned near the face of patient 50 so that it is exposed to the patient's exhaled breath. In this example, the pH of the patient's breath can be continuously monitored. Extending from the sensor 10 are the Antimony sensor electrical communication means 26 and silver chloride reference electrical communication means 28 which are connected to display/processing means 40. The sensor can provide an immediate reading of the pH of the patient's breath or the sensor could be used to measure the pH of the patient's breath for a period of time to monitor and diagnose certain respiratory conditions. Another potential use of the sensor 10 in clinical applications is to detect the absence of breath, a condition known as sleep apnea.

While the invention has been described in detail and with reference to specific embodiment thereof, it will be apparent to one skilled in the art that various changes and modifications can be made therein without departing from the spirit and scope thereof.

I claim:

1. A self-condensing sensor assembly for monitoring pH:
   An outer tubular member;
   an inner tubular member, said outer tubular member co-linearly enclosing an inner tubular member;
   an antimony sensor enclosed within said inner tubular member;
   a reference element enclosed within said outer tubular member and located in a proximal position to said antimony sensor;
   a wick material, said wick material having one side which partially surrounds and substantially engages a portion of said inner tubular member, said wick material extending from said antimony sensor to a proximal position whereby said wick material is substantially engaged to said reference element;
   an ion conduction fluid entrained or retained within said wick material; and
   said self-condensing sensor having the capability to establish an electrical connection via micro-droplets condensed across said antimony sensor and said reference element.

2. The sensor as recited in claim 1, wherein said wick material is selected from the group consisting of fibrous polymeric meshes of polyester, polyimide, polyethylene, polypropylene, polyvinyl chloride, polystyrene, ABS, nylon, acetal, or polyethylene terephthalate (PET), polytetrafluoroethylene (PTFE) or any combinations thereof.

3. The sensor as recited in claim 1, wherein said ion conduction fluid contains a polysaccharide based material.

4. The sensor as recited in claim 1, wherein said ion conduction fluid comprises an electrolyte/water base gel.

5. The sensor as recited in claim 1, wherein said reference element comprises silver chloride.

6. The sensor as recited in claim 1, wherein said reference element comprises a silver element having a silver chloride coating.

7. The sensor as recited in claim 1, wherein said co-linear configuration between said outer tubular member and said inner tubular member are offset.

8. The sensor as recited in claim 1, further comprising an electrical and display means which is in communication with the sensor and processes information obtained from said sensor for presenting a pH reading.

9. A self-condensing sensor assembly for monitoring pH:
   An outer tubular member;
   an inner tubular member, said outer tubular member coaxially enclosing an inner tubular member;
   an antimony sensor enclosed within said inner tubular member and substantially engaged to said inner surface of said inner tubular member, said antimony sensor including an electrical communication which extends to a proximal terminal position;
   a reference element enclosed within said outer tubular member and located proximal to said antimony sensor, said reference sensor element includes an electrical communication which extends to the proximal terminal position;
   a wick material, said wick material having one side which partially surrounds and substantially engages a portion of said inner tubular member, said wick material extending from said antimony sensor to a proximal position whereby said wick material is substantially engaged to said reference element;
   an ion conduction fluid is entrained or retained within said wick material; and
   said self-condensing sensor having the capability to establish an electrical connection via micro-droplets condensed across said antimony sensor and said reference element.

10. The sensor as recited in claim 9, wherein said wick material is selected from the group consisting of fibrous polymeric meshes of polyester, polyimide, polyethylene, polypropylene, polyvinyl chloride, polystyrene, ABS, nylon, acetal, or polyethylene terephthalate, (PET) polytetrafluoroethylene (PTFE) or any combinations thereof.

11. The sensor as recited in claim 9, wherein said ion conduction fluid contains a polysaccharide based material.

12. The sensor as recited in claim 9, wherein said ion conduction fluid comprises an electrolyte/water base gel.

13. The sensor as recited in claim 9, wherein said reference element comprises silver chloride.

14. The sensor as recited in claim 9, wherein said reference element comprises a silver element having a silver chloride coating.

15. The sensor as recited in claim 9, wherein said co-linear configuration between said outer tubular member and said inner tubular member are offset.

16. The sensor as recited in claim 9, further comprising an electrical connector on the proximal end of said sensor, said electrical connector is connected to said electrical communication with the antimony sensor and the reference element.

17. The sensor as recited in claim 9, further comprising a display means which is in electrical communication with the antimony electrical communication and the reference element electrical communication; said display may further processes information obtained from said sensor for presenting pH data in digital or in an analog format.

18. The system as recited in claim 9, wherein said electrical communication is accomplished by a plurality of wires.

19. The system as recited in claim 9, wherein said electrical communication is accomplished by a wireless means.

20. A self-condensing sensor assembly for monitoring pH:
An outer tubular member;
an inner tubular member, said outer tubular member coaxially enclosing an inner tubular member;
an antimony sensor enclosed within said inner tubular member;
a reference element enclosed within said outer tubular member and located in a proximal position to said antimony sensor;
a wick material, said wick material having one side which partially surrounds and substantially engages a portion of said inner tubular member, said wick material extending from said antimony sensor to a proximal position whereby said wick material is substantially engaged to said reference element;
an ion conduction fluid entrained or retained within said wick material; and
said self-condensing sensor having the capability to establish an electrical connection via micro-droplets condensed across said antimony sensor and said reference element.

21. A self-condensing sensor assembly for monitoring pH:
An outer tubular member;
an inner tubular member, said outer tubular member co-linearly or coaxially enclosing an inner tubular member;
an antimony sensor enclosed within said inner tubular member;
a reference element enclosed within said outer tubular member and located in a proximal position to said antimony sensor;
a wick material, said wick material having one side which partially surrounds and substantially engages a portion of said inner tubular member, said wick material extending from said antimony sensor to a proximal position whereby said wick material is substantially engaged to said reference element;
an ion conduction fluid entrained or retained within said wick material,
said wick material and said antimony sensor are positioned at a terminal end of said outer tubular member;
said sensor assembly being of a mass capable of rapidly changing temperature such that it functions to cool below the dew point of exhaled breath and subsequently condenses humid patient breath in close proximity to said sensor to form a liquid on said terminal end; and
said self-condensing sensor having the capability to establish an electrical connection via micro-droplets condensed across said antimony sensor and said reference element.

* * * * *